Figure 1:
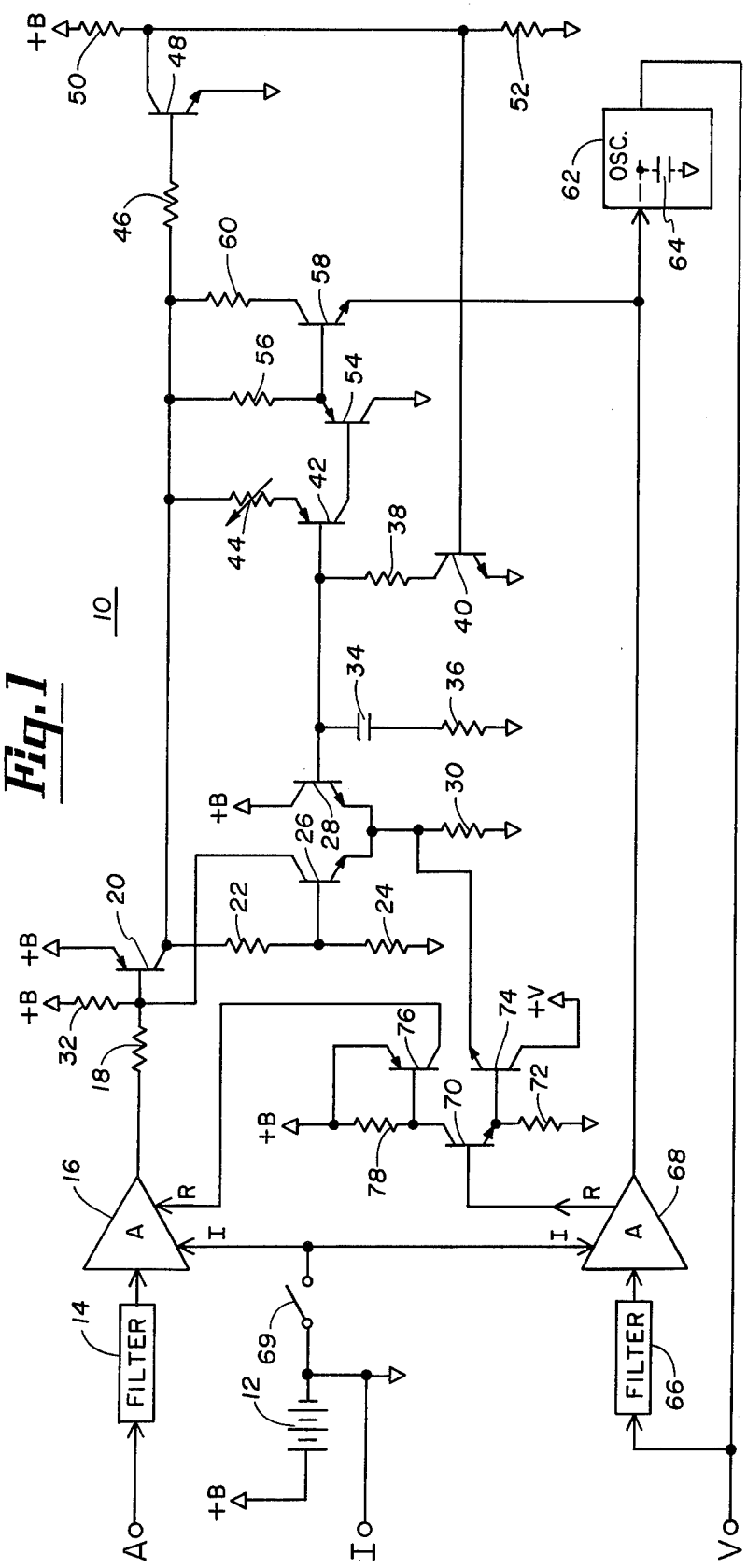

United States Patent [19]

Lin et al.

[11] 4,060,090

[45] Nov. 29, 1977

[54] VARIABLE P-R INTERVAL PACEMAKER

[75] Inventors: Heh-Sen Lin, Brooklyn Center, Minn.; John M. Adams, Mesa, Ariz.

[73] Assignee: Medtronic, Inc., Minneapolis, Minn.

[21] Appl. No.: 663,690

[22] Filed: Mar. 4, 1976

[51] Int. Cl.[2] .............................................. A61N 1/36
[52] U.S. Cl. .............................................. 128/419 PG
[58] Field of Search ................ 128/419 PG, 421, 422, 128/423

[56] References Cited

U.S. PATENT DOCUMENTS

| | | | |
|---|---|---|---|
| 3,253,596 | 5/1966 | Keller, Jr. | 128/419 PG |
| 3,648,707 | 3/1972 | Greatbatch | 128/419 PG |
| 3,693,626 | 9/1972 | Cole | 128/419 PG |
| 3,927,677 | 12/1975 | Gobeli et al. | 128/419 PG |

OTHER PUBLICATIONS

Bonnabeau et al., "Biomedical Sciences Instrumentation," vol. 1, 1963, pp. 407–419.

*Primary Examiner*—William E. Kamm
*Attorney, Agent, or Firm*—Harry W. Barron; Joseph F. Breimayer

[57] ABSTRACT

A pacemaker has circuitry which allows the time between the detection of an atrial contraction and the provision of an electrical stimulus to cause a ventricular contraction to vary with the rate of the sensed atrial contractions. The circuitry includes a differential amplifier having a reference voltage applied to one input and a capacitor coupled to the second input. The capacitor is charged from the time the atrial contraction is sensed to the time the charge equals the reference voltage, at which time the electrical stimulus is provided and the capacitor is discharged between the time the electrical stimulus is provided and the next atrial contraction is sensed. As the heart rate increases, the time between the atrial contractions decreases, and thus the capacitor discharges for a shorter time, or in other words, to a larger voltage and the time required for the capacitor to recharge to the reference voltage becomes less.

10 Claims, 2 Drawing Figures

VARIABLE P-R INTERVAL PACEMAKER

This invention relates to artificial cardiac stimulation and more particularly, to a device for providing an electrical stimulating pulse to stimulate the ventricle portion of the heart to contract at a time after the atrial contraction dependent upon the rate of atrial contractions.

In the prior art, as typified by U.S. Patent Application Ser. No. 648,352, filed Jan. 12, 1976, which is a continuation of Application Serial Number 530,799, filed Dec. 9, 1974, now abandoned, in the name of John Adams and entitled SYNCHRONOUS PACEMAKER WITH UPPER RATE STABILIZATION, which patent application is assigned to the present assignee hereof, a pacemaker circuit is disclosed in which an electrical stimulating pulse is applied to the ventricle of the heart at a fixed time after the sensing of the atrial contraction, if no naturally occurring contraction of the ventricle occurs. This fixed time limitation on the application of the electrical stimulating pulse can operate in a disadvantageous manner when the heart rate is very high, due to for instance tachycardia or physical exertion, because, as the heart rate increases, the time between atrial and ventricular contractions becomes shorter. However, in a situation where a patient suffers from heartblock, the fixed time between the sensing of the atrial contraction and the application of the electrical stimulating pulse remains fixed, thereby causing the ventricular contraction to occur later in the cycle than is desired,.

In accordance with one aspect of this invention, there is provided, in a cardiac pacemaker which provides an electrical stimulus to the ventricle after the sensing of an atrial contraction, an improvement comprising means responsive to the rate of atrial contractions for affecting the time between the sensing of the atrial contraction and the provision of such electrical stimulus to the ventricle.

Figure 2:
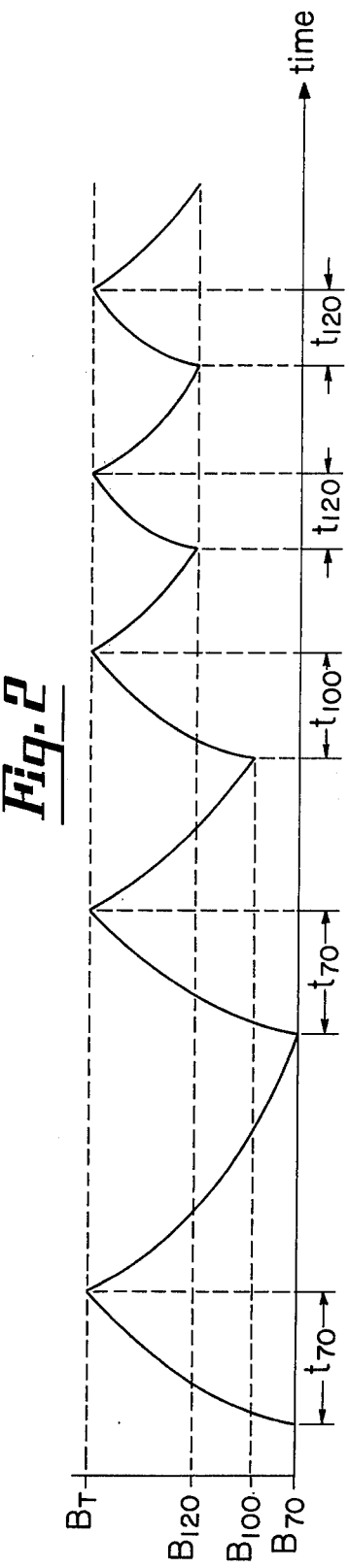

One preferred embodiment of this invention is described hereafter with reference being made to the following Figures, in which, FIG. 1 shows a circuit diagram of the variable P-R time interval atrial synchronous ventricular inhibited pacemaker; and FIG. 2 shows a waveform useful and understand the operation of the circuit of FIG. 1.

Referring now to FIG. 1, a variable PR time interval atrial synchronous ventricular inhibited pacemaker circuit 10 is shown. As with all atrial synchronous pacemakers, a lead is attached to both the atrial and ventricle portions of the heart, which leads are respectively designated as A and V in FIG. 1. In addition, an indifferent plate, which may be a portion of the pulse generator package of of the pacemaker, is labeled I. Indifferent electrode I is coupled to the negative terminal of the d.c. batteries 12 included in the package, and serves as the system ground. The positive terminal of batteries 12 constitutes the source of positive voltage +B.

Each of the terminals A and V serve as electrical signal carrying means which transmit to circuit 10, the electrical signals resulting from the atrial and ventricle contractions within the heart. In addition, the V lead interconnecting the ventricle of the heart and circuit 10 serves a second function of carrying signals from circuit 10 to stimulate the ventricle.

The voltage sensed due to an atrial contraction is applied through the A lead to a filter circuit 14, which filters out other electrical signals within the heart as well as artifacts and noise and allows only a pulse to be applied to amplifier 17 representative of an atrial contraction, or the P wave of an electrocardiac signal. Amplifier 16 includes amplifying and filtering means as well as a refractory means. The function of the refractory means is to inhibit the provision of any subsequent signals for a fixed time after the provision of a first signal by amplifier 16. An example of amplifier 16 is shown in the above-mentioned U.S. patent application Ser. No. 648,352.

The output signal from amplifer 16 is a negative going signal which is applied through resistor 18 to the base of transistor 20 and causes transistor 20 to become conductive. The conduction of transistor 20 causes current to flow from source +B connected to the emitter of transistor 20 through resistors 22 and 24 to ground. The junction of resistors 22 and 24 thus becomes a point of reference voltage which is applied to the base of transistor 26. Transistor 26 is one-half of a differential amplifier or comparator, the other half of which is transistor 28. The emitters of transistors 26 and 28 are coupled together and through resistor 30 to ground. The collector of transistor 28 is coupled to positive voltage +B and the collector of transistor 26 is coupled to the base of transistor 20. In addition, the base of transistor 20 is coupled through resistor 32 to the source of positive voltage +B.

Capacitor 34 is connected in series with resistor 36 between the base of transistor 28 and ground. In addition, the base of transistor 28 is coupled through resistor 38 to the collector of transistor 40, the emitter of which is coupled to ground. Finally, the base of transistor 28 is connected to the base of transistor 42, the emitter of which is coupled through variable resistor 44 to the collector of transistor 20.

In this circuit connection, capacitor 34 is charged as long as transistor 20 is conductive through a path from the collector of transistor 20 through resistor 44 and the emitter-base path of transistor 42. As will be explained hereafter, when transistor 20 becomes nonconductive, transistor 40 becoms conductive and capacitor 34 discharges through resistor 38, the collector-emitter path of transistor 40 and resistor 36. The voltage stored by capacitor 34 is applied to the base of transistor 28 and compared with the base voltage applied to transistor 26, that is, the voltage at the junction of transistors 22 and 24. When the base voltage of transistor 28 exceeds the base voltage applied to transistors 26, transistor 26 ceases conducting and transistor 28 becomes conductive. When transistor 26 ceases conducting, the voltage at the base of transistor 20 becomes high, thereby causing transistor 20 to cease conducting and thus causing the voltage at the collector of transistor 20 to approach ground voltage.

The collector of transistor 20 is also coupled through resistor 46 to the base of transistor 48. The collector of transistor 48 is coupled to the junction of resistor 50 and resistor 52. The other ends of resistor 50 is coupled to the source of positive voltage +B and the other end of resistor 52 is coupled to ground. The emitter of transistor 48 is also coupled to ground. As long as transistor 20 is conductive, transistor 48 is conductive. When transistor 20 becomes nonconductive due to the voltage on capacitor 34 exceeding the voltage at the junction of resistors 22 and 24, transistor 48 becomes nonconductive, thereby causing the voltage between the junctions of resistors 50 and 52 to become high. This, in turn, causes transistor 40 to conduct and allow the voltage stored by capacitor 34 to discharge.

The conductivity of transistor 42 is determined by the voltage stored by capacitor 34. The collector of transistor 42 is connected to the base of transistor 54. The collector of transistor 54 is connected to ground and the emitter of transistor 54 is coupled through resistor 56 to the collector of transistor 20. In addition, the emitter of transistor 54 is coupled to the base of transistor 58. The collector of transistor 58 is coupled through resistor 60 to the collector of transistor 20 and the emitter of transistor 58 is connected to the input of oscillator 62.

Oscillator 62 may be a conventional oscillator used in pacemaker circuits and is described in the above-mentioned U.S. patent application Ser. No. 648,352. In summary, oscillator 62 includes a capacitor 64 which is charged at a time constant determined by internal components thereof, such that after a fixed period of time, which may be approximately 0.855 seconds, capacitor 64 has charged to a predetermined voltage, which is sensed, with the result that an electrical pulse is applied from the output of oscillator 62 through the V lead to the ventricle of the heart to cause the electrical stimulation necessary for a contraction. The emitter of transistor 58 is connected to the charging side of capacitor 64 in oscillator 62, so that, as transistor 58 is rendered more conductive, the charge stored by capacitor 64 equals the transistor 58 emitter voltage, rather than the voltage to which it is charged through the internal charging circuit in oscillator 62.

The operation of that portion of the circuit thus far described will now be explained. When the atrium contracts, an electrical signal (the P wave) is provided through the A lead and filter 14 to amplifier 16, which amplifies the signal and provides a negative going signal through resistor 18 to the base of transistor 20. This signal causes transistor 20 to become conductive, thereby applying a reference voltage between the junction of resistors 22 and 24. At this point, it should be noted that the values of resistors 22 and 24 are selected so that the reference voltage applied to the base of transistor 26 is the same or slightly greater than the voltage to which capacitor 64 charges just prior to a pulse signal being provided from oscillator 62.

The conduction of transistor 20 also causes current to flow through resistor 44 and the emitter-base junction of transistor 42, whereby capacitor 34 begins charging positively at a rate determined by the setting of resistor 44. The voltage at the base of transistor 42 is approximately equal to the voltage at the collector of transistor 42. Thus, as capacitor 34 charges more positively, the voltage at the collector of transistor 42 increases. Because transistors 54 and 58 are connected in an emitter-follower, or common collector, configuration, the voltage at the emitters of these transistors follows closely the voltage at the bases of those transistors. In fact, since transistors 54 and 58 are complementary symmetry transistors, the base-emitter voltage drops cancel one another and thus the voltage at the base of transistor 54 equals the voltage at the emitter of transistor 58. However, it should be noted that if the voltage on capacitor 64 in oscillator circuit 62 increases above the voltage at the base of transistor 58, the emitter voltage will equal the capacitor 64 voltage and not the transistor 58 base voltage, at least until such time as the capacitor 34 voltage exceeds the capacitor 64 voltage.

As previously mentioned the values of resistors 22 and 24 are selected so that the voltage applied to the base of transistor 26 is approximatey equal to the voltage to which capacitor 64 is charged prior to oscillator 62 providing a pulse to the V lead to electrically stimulate the ventricle. When an atrial contraction is sensed and amplified by amplifier 16 and provided to render transistor 20 conductive, capacitor 34 immediately begins charging. The voltage stored by capacitor 34 is reflected through transistors 42, 54 and 58 to the emitter of transistor 58 and causes capacitor 64 to be charged to the voltage. At the time capacitor 34 becomes charged to the voltage applied to the base of transistor 26, the voltage at the emitter of transistor 58 will be sufficient to have charged capacitor 64 to that voltage sufficient to cause oscillator 62 to provide a pulse at its output. In addition, when the voltage across capacitor 34 reaches a voltage applied to the base of transistor 26, transistor 26 ceases conducting and transistor 28 begins conducting. When transistor 26 ceases conducting, the voltage at the base of transistor 20 is no longer clamped to a voltage lower than $+B$ and transistor 20 ceases conducting. This, in turn, causes transistor 48 to stop conducting, which, in turn causes the positive voltage to be applied to the base of transistor 40 rendering transistor 40 conductive. This then allows capacitor 34 to discharge.

It should also be noted that at the time a pulse is provided from oscillator 62 to cause a ventricular contraction, the voltage across capacitor 64 is shorted to ground. Thereafter capacitor 64 will begin charging through the internal charge path within oscillator 62 and after a period of 0.855 seconds will have obtained a charge sufficient to cause oscillator 62 to provide a pulse on its own; unless, of course, the transistor 58 emitter voltage increases to a value sufficient for oscillator 62 to provide a pulse sooner.

Referring now to FIG. 2, a waveform is shown which is useful in understanding the operation of capacitor 34 and the circuitry associated therewith in causing a time variable with rate to occur between the detection of an atrial contraction then the provision of an electrical stimulus to cause a ventricular contraction. For exemplary purposes only, heart beats at the rate of 70 beats per minute, 100 beats per minute and 120 beats per minute, will be discussed. In case of a beat of 70 beats per minute, the time between atrial contractions is 0.855 seconds; for 100 beats per minute the time is 0.60 seconds; and for 120 beats per minute the time is 0.50 seconds.

First with respect to a 70 beats per minute cardiac rate, capacitor 34 is charged to the voltage at the junction of resistors 22 and 24 which in FIG. 2 has been designated as $B_T$. As mentioned, when capacitor 34 is charged to voltage $B_T$, transistor 40 is rendered conductive and capacitor 34 begins discharging until such time as another atrial contraction is sensed, at which time capacitor 34 again is charged to $B_T$ through the emitter-base path of transistor 42. From FIG. 2 it may be observed that the longer the time between atrial contractions, or in other words the lower the heart rate, the more capacitor 34 discharges. The rate of discharge of capacitor 34 of course is determined by the time constant of resistor 36 plus resistor 38 times the capacitance of capacitor 34. In FIG. 2, capacitor 34 discharges to a voltage designated as $B_{70}$. The time required for capacitor to charge from $B_{70}$ to $B_T$ is $t_{70}$.

When the heart rate increases to, for instance, 100 beats per minute, capacitor 34 will discharge to a voltage $B_{100}$, which is greater than voltage $B_{70}$ due to the shorter discharge time involved. When the next atrial contraction is sensed, capacitor 34 again begins charging to voltage $B_T$; however, since the voltage at the time charging begins is greater at a 100 beats per minute rate, the time $t_{100}$ required for capacitor to charge to voltage $B_T$ is less than time $t_{70}$. Again from FIG. 2 it is seen that when the rate increases to 120 beats per minute, capacitor 34 only discharges to a voltage $B_{120}$, which is greater than both $B_{100}$ and $B_{70}$. Thus, the time $t_{120}$ required to charge from $B_{120}$ to $B_T$ is less than time $t_{100}$ or in other words, the ventricular stimulus is provided at a shorter time after the atrial contraction sensing.

Referring again to FIG. 1, a description is hereafter given on the remaining elements of circuit 10 which allow circuit 10 to operate within an atrial synchronous ventricular inhibited pacemaker. The V electrode is connected to a filter circuit 66, which may be designed to pass only the ventricular contraction electrical signals, or R waves, to an amplifier 68. Both amplifiers 16 and 68 include an inhibit input both of which are connected together and to one end of switch 69, the other end of which is connected is system ground. When switch 69 is closed, both amplifier 16 and amplifier 68 are disabled and oscillator 62 provides pulses at the rate internally set by the charging of capacitor 64 therein. Switch 69 may be closed in a known manner magnetically by a physician desiring to check the rate and pulse width of the pulses provided by oscillator 62. This checking by the physician enables him to determine the proper operation of the pacemaker and the life remaining in the battery system 12 thereof.

When a ventricular contraction occurs, and is sensed by amplifier 68, the output therefrom is a ground level voltage, which is applied directly to the input of oscillator 62. At the same time, a signal is provided from the refractory output of amplifier 68 to the base of transistor 70. The emitter of transistor 70 is connected through a resistor 72 to ground. In addition, the emitter of transistor 70 is connected to the base of transistor 74. The collector of transistor 74 is connected to positive voltage +B and the emitter of transistor 74 is connected to the junction between the emitters of transistors 26 and 28 and resistor 30.

The collector of transistor 70 is connected to the base of transistor 76, the emitter of transistor 76 is connected to the source of positive voltage +B and in addition, the emitter of transistor 76 is coupled through resistor 78 to the base of transistor 76. The collector of transistor 76 is coupled to the refractory input of amplifier 16 to cause amplifier 16 to be refractory to any signals applied thereto for the refractory time thereof, or in other words, amplifier 16 is inhibited from sensing any atrial contraction signals during the refractory time period.

In operation, when a ventricular contraction is sensed as a signal on the V lead, a signal is provided from the refractory output of amplifier 68 to render transistor 70 conductive, which, in turn, causes positive voltage to be applied to the base of transistor 74 to render it conductive. Thus, a positive voltage is applied to the junction of the emitters of transistors 26 and 28 and renders them both nonconductive. When this occurs transistor 20 becomes nonconductive and transistor 40 becomes conductive allowing capacitor 34 to discharge. In addition, transistors 42, 54 and 58 are rendered nonconductive.

In addition, when transistor 70 becomes conductive, the voltage at the base of transistor 76 falls to the value determined by resistors 72 and 78 and transistor 76 becomes conductive, thereby causing amplifier 16 to become refractory to any atrial contractions occurring during the refractory period.

When transistor 58 ceases conducting due to the cessation of conduction of transistor 20, the ground voltage at the output of amplifier 68 allows capacitor 64 within oscillator 62 to discharge with a short time constant. In this manner, oscillator 62 is reset so that 0.855 seconds later capacitor 64 will again have charged to a voltage that causes oscillator 62 to provide a pulse, unless the voltage at the emitter of transistor 58 causes capacitor to be charged to such a voltage at an earlier time.

It should be noted that the signal activating the amplifier 68 action, can be either a normal ventricular contraction, such as the R wave of an electrocardiac signal, or a premature ventricular contraction (PVC). In either event, it is not desired to provide the electrical stimulus to the heart and accordingly, the entire circuit 10 is turned off and capacitor 64 discharged.

Connected in a manner just described, circuit 10 can operate in any one of seven different modes depending on the fact and circumstances of the patient's cardiac action. The seven modes are: (1) Inhibited mode in which the patient has a heart rate greater than 70 beats per minute and a naturally occurring ventricular contraction at a time less than the time required for capacitor 34 to charge to the voltage $B_T$; (2) PVC Inhibited mode, in which a PVC inhibits all operations of circuit 10; (3) Demand mode where the heart rate is less than 70 beats per minute; (4) P-Wave Synchronous mode in which the heart's atrial beat rate is between 70 and 120 beats per minute; (5) Upper Rate Limit mode in which the heart's atrial beat is between 120 and 160 beats per minute; (6) Asynchronous mode in which switch 69 is closed allowing oscillator 62 to operate independently of the remaining portion of the circuit; and (7) Protection mode in which the atrial rate exceeds 160 beats per minute.

In the Inhibited mode and PVC Inhibited mode, amplifier 68 detects the naturally occurring ventricular contraction or a premature ventricular contraction and provides a ground level signal to allow the capacitor 64 to discharge, while providing signals through transistors 70, 74 and 76 to reset the remaining portions of circuit 10 and to cause amplifier 16 to become refractory. In the Demand mode, capacitor 64 in oscillator 62 charges to the value necessary to allow oscillator 62 to provide an electrical stimulating signal every 0.855 seconds. In the P-Wave Synchronous mode, amplifier 16 detects atrial contractions and causes capacitor 34 to begin charging, while at the same time rendering transistors 42, 54 and 58 conductive to allow capacitor 64 to be charged by the voltage at the emitter of transistor 58 until such time as oscillator 62 provides a pulse due to the voltage on transistor 58. It is within this mode that the variable time action of the capacitor 34 and associated circuitry is most beneficial from a physiological point of view. The Upper Rate Limit mode of operation is explained in detail in the aforementioned U.S. patent application Ser. No. 648,532 and operates by causing selected atrial contractions, which are sensed by amplifier 16, to have no electrical stimulating pulse provided through the V lead so as to maintain the rate of ventricular stimulating pulses at approximately 120 per minute. Again with this mode of operation, the variable time provided by capacitor 34 and the associated circuitry is important. The Asynchronous mode is utilized by the physician causing switch 69 to close to determine the rate at which oscillator 64 will provide pulses without any of the effects of the remaining portions of the circuitry. The Protection mode is entered when the heart-'atrial rate exceeds 160 beats per minute and causes oscillator 62 to provide pulses at a constant rate of 120 beats per minute.

What is claimed is:

1. In a cardiac pacemaker having means for providing an electrical stimulus to the ventricle after the sensing of an atrial contraction, the improvement comprising means responsive to the rate of atrial contractions for affecting the time between the sensing of an atrial contraction and the provision by said providing means of said electrical stimulus to the ventricle, said affecting means including a two input comparator circuit, a first input circuit coupled to one comparator input for maintaining that one input at a reference value and a second input circuit for providing a value to be compared with said reference value to the other input of said comparator circuit, said second input circuit including a variable value providing means for providing a value which increases at a first rate to said reference value from the time each atrial contraction is sensed and which decreases at a second rate from each time said reference value is reached until the next atrial contraction is sensed.

2. In a cardiac pacemaker having means for providing an electrical stimulus to the ventricle after the sensing of an atrial contraction, the improvement comprising means responsive to the rate of atrial contractions for affecting the time between the sensing of an atrial contraction and the provision by said providing means of said electrical stimulus to the ventricle, said affecting means including differential amplifier means, reference voltage providing means coupled to one input of said differential amplifier means, energy storage means coupled to provide a voltage manifesting stored energy to the other input of said differential amplifier, switching means coupled to said reference voltage providing means and said energy stored means for being switched to a first state in response to the sensing of an atrial contraction, said reference voltage providing means responding to said first state of said switching means by providing a reference voltage to said one input of said differential amplifier, said energy storage means responding to said first state of said switch means by increasing the energy stored thereby at a first rate, said switching means remaining in said first state until said voltage provided by said energy storage means equals said reference at which time said switching means responds by switching to a second state, and energy storage means responding to said second state of said switching means by discharging energy at a second rate, which second rate is less than said first rate.

3. A cardiac pacemaker comprising means for providing an electrical stimulus to the ventricle after having sensed an atrial contraction; and means responsive to the rate of atrial contractions for affecting the time between the sensing of an atrial contraction and the provision by said providing means of said electrical stimulus to the ventricle;
said electrical stimulus providing means including oscillator means having energy storage means which increasingly stores energy at a first rate until energy of a certain value has been stored, whereupon a pulse is provided and the energy stored by said energy storage means decrease to a reference value at a second rate, which second rate is much greater than said first rate; and
wherein said affecting means is coupled to said energy storing means for causing the energy stored by said energy storing means to be at said certain value at a time dependent upon said rate of atrial contractions.

4. The invention according to claim 3 wherein said affecting means includes a two input comparator means having a reference voltage switchably applied to one input thereof and further having a capacitor coupled to the other input thereof, said capacitor being switchably charged and discharged to provide a voltage to said other input that is compared with said reference voltage;

switch means for entering a first state in response to the sensing of an atrial contraction, said reference voltage being applied and said copacitor being charged during said first state, said comparator being coupled to said switch means to cause said switch means to enter a second state in response to said capacitor being charged to said reference voltage, said reference voltage not being applied and said capacitor discharging during said second state; and means for applying the voltage stored by said capacitor to said oscillator means during the time said switching means is in said first state to cause said oscillator means to provide a pulse when said capacitor becomes charged to said reference voltage.

5. An atrial synchronous, ventricular inhibited pacemaker circuit for providing an electrical stimulus to a lead coupled to the ventricle of a heart at a time dependent on the rate of sensed electrical signal on a lead coupled to the atrium of said heart, each of which sensed signal manifests an atrial contraction, said circuit comprising:

means for sensing said electrical signal on said lead coupled to said atrium;

switch means coupled to said sensing means for entering a first state in response to said sensing means sensing said electrical signal on said lead coupled to said atrium;

comparator means having a first input, a second input and an output, said output being coupled to said switching means to provide a signal to said switching means upon the voltage at said second input equaling the voltage at said first input, said switching means responding to said signal by entering a second state;

means for providing a first reference voltage to said first comparator means input during the time said switching means is in said first state;

first capacitive means coupled to said second comparator means input;

means for providing a voltage to said first capacitive means while said switching means is in said first state to cause said first capacitive means to become charged, and thereby provide a voltage to said second comparator input;

discharge path means responsive to said switching means being in said second state for switchably connecting a discharge path to said first capacitive means;

oscillator means including second capacitive means which is charged to a second reference voltage over a given first time period and then discharged during a second time period, which is much less than said first time period;

means for providing an electrical stimulus to said lead coupled to said ventricle upon sensing said second capacitive means has been charged to said second reference voltage; and means for providing a voltage related to the voltage to which said first capacitive means has charged to charge said second capacitive means.

6. The invention according to claim 5 wherein said relation between said voltage to which said first capacitive means is charged and the voltage applied by said last mentioned means to said second capacitive means is such that when said first capacitive means is charged to said first reference voltage, said second capacitive means will be charged to said second reference voltage.

7. The invention according to claim 6 wherein said first reference voltage equals or slightly exceeds said second reference voltage.

8. The invention according to claim 5:

wherein said comparator means is a differential amplifier; and wherein said switching means is a transistor which is initially rendered conductive by a sensed signal on the atrium lead and maintained conductive by the output signal from one side of said differential amplifier.

9. The invention according to claim 5 wherein said circuit further comprises:

means for sensing the occurrence of an electrical signal on said ventricle lead caused by a ventricular contraction of the heart and for providing a signal manifesting such signal sensing;

means for providing said signal to said comparator means and said oscillator means, said comparator means and said oscillator means, said comparator means responding to said ventricle lead sensing means signal by providing a signal to said switching means to which said switching means responds by entering said second state, said oscillator means responding to said ventricle lead sensing means signal by said second capacitive means discharging.

10. The invention according to claim 9 wherein said means for sensing said atrial lead signals includes refractory means for preventing the sensing of a subsequent signal during a certain refractory time period; and wherein said means for sensing said ventricle lead signals includes means coupled to said means for sensing atrial lead signals to activite said refractory means to commence said refractory time.

* * * * *